United States Patent [19]
Geiger

[11] Patent Number: 5,250,810
[45] Date of Patent: Oct. 5, 1993

[54] MID-INFRARED LIGHT HYDROCARBON DIAL LIDAR

[75] Inventor: Allen R. Geiger, Las Cruces, N. Mex.

[73] Assignee: LaSen, Inc., Las Cruces, N. Mex.

[21] Appl. No.: 872,306

[22] Filed: Apr. 23, 1992

Related U.S. Application Data

[63] Continuation of Ser. No. 539,230, Jun. 18, 1990, Pat. No. 5,157,257.

[51] Int. Cl.$^5$ ............................................. G01N 21/35
[52] U.S. Cl. .................................. 250/338.5; 250/339
[58] Field of Search ............................. 250/338.5, 339

[56] References Cited

U.S. PATENT DOCUMENTS

| | | | |
|---|---|---|---|
| 3,766,380 | 10/1973 | Menzies | 250/343 |
| 3,953,792 | 4/1976 | Fletcher et al. | 324/61 |
| 4,143,338 | 3/1979 | Godard et al. | 331/94.5 C |
| 4,394,573 | 7/1983 | Correa et al. | 250/253 |
| 4,397,549 | 8/1983 | Morgan | 356/5 |
| 4,426,640 | 1/1984 | Becconsall et al. | 250/338.5 |
| 4,434,364 | 2/1984 | Correa et al. | 250/253 |
| 4,450,356 | 5/1984 | Murray et al. | 250/339 |
| 4,489,239 | 12/1984 | Grant et al. | 250/338.5 |
| 4,490,043 | 12/1984 | Cramp | 356/407 |
| 4,687,337 | 8/1987 | Stewart et al. | 356/437 |
| 4,696,012 | 9/1987 | Harshaw | 372/99 |
| 4,820,914 | 4/1989 | Allen | 250/207 |

FOREIGN PATENT DOCUMENTS

808760 3/1969 Canada ............................ 250/339

OTHER PUBLICATIONS

Baumgartner et al., "Continuously Tunable IR Lidar with Applications to Remote Measurements of SO$_2$ and CH$_4$", Applied Optics, 17 (22), pp. 3555-3561, Nov. 1978.

Browell et al., "Airbourne Differential Absorption Lidar System for Water Vapor Investigations", Optical Engineering, 20 (1), Jan./Feb. 1981, pp. 84-90.

Reid et al., "High Sensitivity Pollution Detection Employing Tunable Diode Lasers", Applied Optics, 17 (2), Jan. 1978, pp. 300-307.

*Primary Examiner*—Carolyn E. Fields
*Attorney, Agent, or Firm*—Kramer, Brufsky & Cifelli

[57] ABSTRACT

A DIAL LIDAR system, and methods of operating same are disclosed. A plurality, such as six, distinct coherent beams are combined into a single transmitted beam. Atmospheric targets, such as light hydrocarbons cause a portion of the transmitted beam to be reflected as a return. In one transmitting configuration, six pulsed beams are fully time-multiplexed, and are combined through selective polarization. In another transmitting configuration, six pulsed beams are fully time-multiplexed, and are combined through selective orientation of beam paths, in connection with a rotating beam displacer. In yet another transmitting configuration, six beams are wavelength-multiplexed, and are combined through differential refraction. In one receiving configuration, time-multiplexed beams are received using a single detector. In another receiving configuration, wavelength-multiplexed beams are received using multiple detectors. In a coherent LIDAR configuration, the outputs of a plurality of coherent sources are modulated, and combined according to any of the aforementioned transmitting configurations. A portion of the source outputs is directed to a receiver section of the system, where it is used to demodulate the LIDAR return.

9 Claims, 10 Drawing Sheets

MID-INFRARED LIGHT HYDROCARBON DIAL LIDAR

This application is a continuation of application Ser. No. 07/539,230, filed Jun. 18, 1990, now U.S. Pat. No. 5,157,257.

TECHNICAL FIELD OF THE INVENTION

The invention relates to a differential absorption laser (DIAL), light detection and ranging (LIDAR) laser system and, more particularly, to a system for detecting light hydrocarbons in the atmosphere.

BACKGROUND OF THE INVENTION

U.S. Pat. No. 4,450,356 discloses remotely detecting gases in the atmosphere by using a frequency-mixed $CO_2$ laser beam formed by passing the beam from a first $CO_2$ laser through a frequency doubler and then frequency-adding the output to the frequency from a second $CO_2$ laser to obtain wavelengths in the 3 micron region. A first wavelength in this region, preselected for nonabsorption by the gases to be detected, is transmitted through the gases toward an object capable of reflecting the beam back. A second wavelength preselected as highly absorbed by the gases to be detected is then transmitted. The presence and quantity of the gases is then determined by the difference in the amount respectively absorbed at the two wavelengths.

U.S. Pat. No. 4,490,043 discloses laser scanning apparatus for monitoring of gaseous pollutants (e.g. in a chemical plant) in which two laser beams having different wavelengths (one corresponding to an absorption line of the gas to be monitored) and modulated at different frequencies are combined into a single scanning beam. A portion of the scattered radiation is collected, detected and measured to give, for each chosen beam direction, the amount of the gas being monitored. The amount of radiation reaching the detector from the laser source is varied according to a predetermined program or in response to an external stimulus, and by this means the detector can be protected against severe overload when the beam scans over positions of abnormally high reflectivity.

U.S. Pat. No. 4,489,239 discloses a portable laser system for remote detection of methane gas leaks and concentrations. The system transmitter includes first and second lasers, tuned respectively to a wavelength coincident with a strong absorption line of methane and a reference wavelength which is weakly absorbed by methane gas. The lasers are aimed at a topographical target along a system axis and the beams successively interrupted by a chopper wheel. The system receiver includes a spherical mirror for collecting the reflected laser radiation and focusing the collected radiation through a narrowband optical filter onto an optial detector. The filter is tuned to the wavelength of the two lasers, and rejects background noise to substantially improve the signal-to-noise ratio of the detector. The output of the optical detector is processed by a lock-in detector synchronized to the chopper, and which measures the difference between the first wavelength signal and the reference wavelength signal.

In the 3.0 to 3.5 micron region there are atmospheric absorption features. Water is the dominant molecular absorber in this region with trace absorption due to carbon dioxide. Ideally one would like to get all of one's laser energy to the target area, i.e., 100% transmission. However, in the lower atmosphere at ranges greater than one km (kilometer), less than 100% of the transmitted energy makes it to one kilometer. The amount of loss that is acceptable is determined by the absorption characteristics of the selected species and the nature, or wavelength extent of the interfering species. Using methane and propane as the target species, these species have absorption features of 80% and 60% respectively. A loss of 50% of the laser energy at one km is not unacceptable. Therefore, there are two windows in the atmosphere between 3.0 and 3.5 microns.

The first is from 3.16 to 3.18 microns and may be suitable for methane detection. The second, is between 3.38 and 3.51 microns, where ethane, propane and butane can be detected. However, water vapor absorption is the dominate absorption feature and a DIAL lidar measures various laser lines for loss. Therefore, a change in the relative humidity will produce a loss in the various laser lines, which is not linear between these lines. But a water vapor correction can be made if the lidar measures water vapor along the beam path.

DISCLOSURE OF THE INVENTION

According to the invention a LIDAR system is provided, especially for detecting the presence of light hydrocarbons in the atmosphere. A plurality, such as six, distinct coherent beams are combined into a single transmitted beam. Atmospheric targets, such as light hydrocarbons cause a portion of the transmitted beam to be reflected as a return. Various transmitting and receiving configurations are disclosed. In one transmitting configuration, six pulsed beams are fully time-multiplexed, and are combined through selective polarization.

In another transmitting configuration, six pulsed beams are fully time-multiplexed, and are combined through selective orientation of beam paths, in connection with a rotating beam displacer.

In yet another transmitting configuration, six beams are wavelength-multiplexed, and are combined through differential refraction.

In one receiving configuration, time-multiplexed beams are received using a single detector.

In another receiving configuration, wavelength-multiplexed beams are received using multiple detectors.

In both receiver configurations, Noise Equivalent Power is maintained at a minimum.

Further according to the invention, a coherent LIDAR system is disclosed. The outputs of a plurality of coherent sources are modulated, and combined according to any of the aforementioned transmitting configurations. The sources are pulsed for the time-multiplexed configurations, and may be continuous wave (CW) for the wavelength-multiplexed configuration. A portion of the source outputs is directed to a receiver section of the system, where it is used to demodulate the LIDAR return.

Hardware configurations and signal processing techniques are disclosed.

The disclosed LIDAR system is designed to operate in two atmospheric spectral windows, 2.0–2.4 microns or 3.1 to 3.5 microns. The 2.0 micron region is not considered to be of prime importance, however, under certain meteorological conditions there may be advantages to using the 2.0 micron window for methane detection. The 3.1 to 3.5 micron region has two spectral windows, 3.16 to 3.18 microns and 3.37 to beyond 3.5 microns. The 3.1 to 3.5 micron window may be suitable for methane detection while the 3.37 to 3.5 micron region can be used for the heavier hydrocarbon detection.

The various laser lines that are used are affected by various meteorological parameters. Various aerosols and relative humidity affect the various laser lines differently and must be accounted for. This can be done by monitoring the atmospheric water vapor and adding a water correction in the DIAL calculation.

The LIDAR works well under most meteorological condition, operating in rain, snow and moderate dust storms. The LIDAR's performance suffers to the degree that operation may have to stop during periods of heavy rain and fog. The LIDAR operates best under dry cold conditions and less so under hot humid conditions. Some of the meteorological limitations can be overcome by selectively switching from the 3.17 micron band to the 2.2 micron window under extremely high hot and humid conditions.

The LIDAR system design remains in line with the multi-laser line simultaneous transmission concept. In order to achieve the sensitivities required, coherent detection may be employed. However, a multi-line OPO design can perform this function as well.

Other objects, features and advantages of the invention will become apparent in light of the following description thereof.

DETAILED DESCRIPTION OF THE INVENTION

General Considerations

The DIAL LIDAR system of the present invention will operate at the absorption bands of the light hydrocarbons in either the 2.2 to 2.4 micron region or the 3.1 to 3.5 micron region. As discussed previously, the 3.1 to 3.5 micron region is preferred because of the stronger and more distinctive absorption spectra. Also the 3 micron region is a safer region to operate at the pulsed powers required for LIDAR detection of light hydrocarbons at levels below 10 ppb (parts per billion) at ranges of 1 km (kilometer). Both the 2.2 to 2.4 and the 3.1 to 3.5 micron regions are considered atmospheric "windows", i.e., the atmosphere is not opaque to electro magnetic radiation in this region. However, there will be loss of energy in each of these regions due to scattering and absorption.

It is known that the mid-infrared light propagates through the atmosphere better than the visible light because it is scattered less. However, there are more molecular absorbers in the infrared also. Therefore, it is necessary to determine those regions of the two infrared bands where maximum transmissions occur in order to maximize the range limit of the LIDAR.

The window from 3.16 to 3.18 microns lies on a methane absorption feature. This window may be used for methane detection and has been labeled as the 3 micron methane window. The 3.37 to 3.50 region contains some methane features (3.39), however, the heavier hydrocarbons ethane, propane, and butane have strong features in this region so it has been labeled the propane window.

Transmitter Configuration

For the purpose of the LIDAR transmitter, the light at six wavelengths from six separate lasers must be combined into a single beam. That is, the beams must be colocated spatially and be propagating along the same optical axis. The properties of polarization (there are only two linearly independent polarizations), wavelength or frequency, and time-multiplexing of pulsed sources are used to combine the beams and later to separate them. If the pulse width of the source were long enough, or if it were CW, then the amplitude of the signal could be modulated to encode the six wavelengths; but amplitude modulation of a 10 nsec pulse would require an impractically high bandwidth at the receiver to achieve the desired system performance.

FIG. 1A

Figure 1:
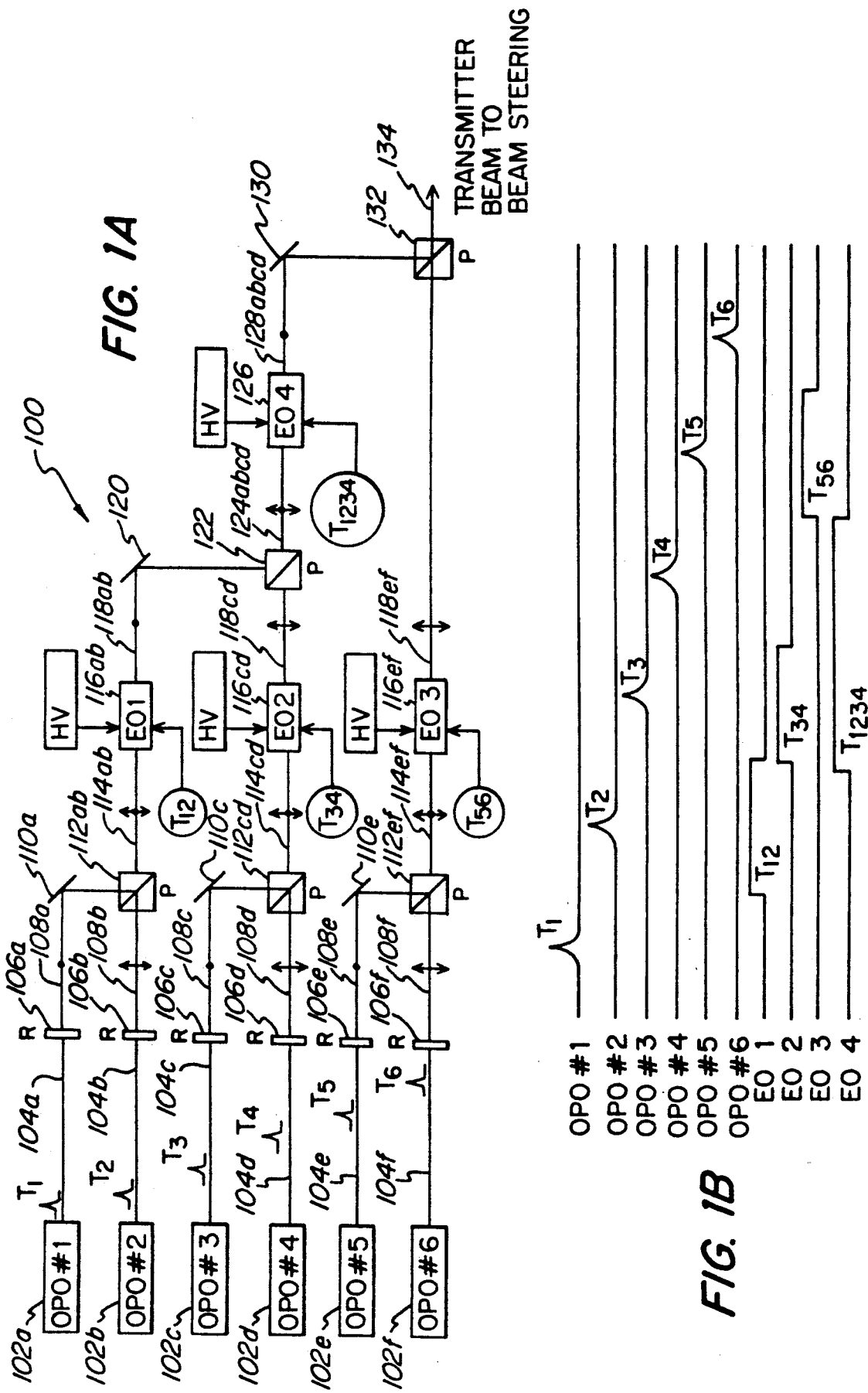
FIG. 1A is a schematic block diagram of a LIDAR transmitter employing a fully time-multiplexed, solid state, high efficiency beam combiner, according to the present invention.
FIG. 1B is a timing diagram of the LIDAR transmitter of FIG. 1A.

FIG. 1A shows a fully time-multiplexed transmitter configuration 100 that uses time encoding of the wavelengths to combine the light at six wavelengths from six lasers into a single beam. It employs a solid state, high efficiency beam combiner, and relies on the polarization state of the beams to implement a switching scheme that alternately directs each of the six pulses to the output with little loss. This scheme has no moving parts and is rugged, but it is rather expensive.

More particularly, six coherent light sources $102a$, $102b$, $102c$, $102d$, $102e$ and $102f$ are pulsed to provide six output beams $104a$, $104b$, $104c$, $104d$, $104e$ and $104f$ at six distinct time intervals $T_1$, $T_2$, $T_3$, $T_4$, $T_5$ and $T_6$. The light sources may be Optical Parametric Oscillators (OPOs), and are labelled OPO#1, OPO#2, OPO#3, OPO#4, OPO#5 and OPO#6. As is evident from the timing diagram of FIG. 1B, the OPOs are pulsed in a predetermined sequence.

The polarized beams from the OPOs are changed into selected linear polarization states with polarization rotators 106a, 106b, 106c, 106d, 106e and 106f, labelled "R", as follows.

The beam 104a from the OPO 102a is given a first polarization, represented by the dot on the beam 108a output by the polarization rotator 106a. The beam 104b from the OPO 102b is given a second, orthogonal polarization, represented by the two-headed arrow on the beam 108b output by the polarization rotator 106b. The beams 108a and 108b constitute a pair of dissimilarly polarized beams.

The beam 104c from the OPO 102c is given a first polarization, represented by the dot on the beam 108a output by the polarization rotator 106c. The beam 104d from the OPO 102d is given a second, orthogonal polarization, represented by the two-headed arrow on the beam 108d output by the polarization rotator 106d. The beams 108c and 108d constitute a pair of dissimilarly polarized beams.

The beam 104e from the OPO 102e is given a first polarization, represented by the dot on the beam 108e output by the polarization rotator 106e. The beam 104f from the OPO 102f is given a second, orthogonal polarization, represented by the two-headed arrow on the beam 108f output by the polarization rotator 106f. The beams 108e and 108f constitute a pair of dissimilarly polarized beams.

The pairs of beams (e.g., 108a and 108b) are combined by polarizing beam splitters, such as cubes or prisms, as follows.

The beam 108a is provided via a mirror 110a to one input of a polarizing beam splitter 112ab, labelled "P". The beam 108b is provided to another input of the beam splitter 112ab. The beam splitter 112ab may be a polarizing cube or prism. The output of the beam splitter 112ab is a beam 114ab having two pulses, one pulse at $T_1$ with the first polarization, and another pulse at $T_2$ with the second polarization, represented by the two-headed arrow with the dot on the beam 114ab.

The beam 108c is provided via a mirror 110c to one input of a polarizing beam splitter 112cd, labelled "P". The beam 108d is provided to another input of the beam splitter 112cd. The beam splitter 112cd may be a polarizing cube or prism. The output of the beam splitter 112cd is a beam 114cd having two pulses, one pulse at $T_3$ with the first polarization, and another pulse at $T_4$ with the second polarization, represented by the two-headed arrow with the dot on the beam 114cd.

The beam 108e is provided via a mirror 110e to one input of a polarizing beam splitter 112ef, labelled "P". The beam 108f is provided to another input of the beam splitter 112ef. The beam splitter 112ef may be a polarizing cube or prism. The output of the beam splitter 112ef is a beam 114ef having two pulses, one pulse at $T_5$ with the first polarization, and another pulse at $T_6$ with the second polarization, represented by the two-headed arrow with the dot on the beam 114ef.

Since the pairs of pulses in each beam 114ab, 114cd and 114ef are separated in time, an electro-optical polarization rotator, such as a Pockels cell, can be used to change the polarization of one of the pulses so that both pulses of the pair are in the same polarization state. More particularly:

A Pockels cell 116ab receives timing pulses (trigger signals) $T_{12}$ that will allow the beam 108a at the first polarization to pass through non-rotated, and that will cause the beam 108b at the second polarization to be rotated 90 degrees to the first polarization. This is represented by the dot on the output 118ab of the Pockels cell. The timing pulse $T_{12}$ is provided by any suitable means, and the Pockels cell 116ab is energized by a high voltage supply, labelled "HV". The timing of the pulse $T_{12}$ is represented on the timing diagram as affecting the rotation of the beam 108b output by the OPO 102b at the time interval $T_2$.

A Pockels cell 116cd receives timing pulses (trigger signals) $T_{34}$ that will allow the beam 108d at the second polarization to pass through non-rotated, and that will cause the beam 108c at the first polarization to be rotated 90 degrees to the second polarization. This is represented by the two headed arrow on the output 118cd of the Pockels cell. The timing pulse $T_{34}$ is provided by any suitable means, and the Pockels cell 116ab is energized by a high voltage supply, labelled "HV". The timing of the pulse $T_{34}$ is represented on the timing diagram as affecting the rotation of the beam 108c output by the OPO 102c at the time interval $T_3$.

A Pockels cell 116ef receives timing pulses (trigger signals) $T_{56}$ that will allow the beam 108f at the second polarization to pass through non-rotated, and that will cause the beam 108e at the first polarization to be rotated 90 degrees to the second polarization. This is represented by the two headed arrow on the output 118ef of the Pockels cell 116ef. The timing pulse $T_{56}$ is provided by any suitable means, and the Pockels cell 116ef is energized by a high voltage supply, labelled "HV". The timing of the pulse $T_{56}$ is represented on the timing diagram as affecting the rotation of the beam 108e output by the OPO 102e at the time interval $T_5$.

The output 118ab of the Pockels cell 116ab at the first polarization (dot) is provided via a mirror 120 to one input of a polarizing beam splitter 122, such as a polarizing cube or prism, and the output 118cd of the Pockels cell 116cd at the second polarization (two-headed arrow) is provided to the other input thereof. The output 124abcd of the beam splitter 122 contains four pulses, two of which are at the first polarization and two of which are at the second polarization, as described above, and is provided to an electro-optical polarization rotator 126, such as a Pockels cell, to select the first polarization, as follows.

The Pockels cell 126 receives timing pulses $T_{1234}$ that will allow the component 118ab of the beam 124abcd at the first (dot) polarization to pass through non-rotated, and that will cause the component 118cd of the beam 124abcd at the second (arrow) polarization to be rotated 90 degrees to the first (dot) polarization. This is represented by the dot on the output 128abcd of the Pockels cell 126. The timing pulse $T_{1234}$ is provided by any suitable means, and the Pockels cell 126 is energized by a high voltage supply, labelled "HV". The timing of the pulse $T_{1234}$ is represented on the timing diagram.

The output of the Pockels cell 126 is provided via a mirror 130 to one input of a beam splitter 132, such as a polarizing cube or prism, and the output 118ef of the Pockels cell 116ef is provided to the other input thereof.

Through this combining and polarization rotating process, all of the beams 104a–104f are combined in the output beam 134, which is provided to a suitable beam steering mechanism (not shown) for transmission into the atmosphere.

At the wavelengths of interest, quartz crystals can be used for the polarization rotators and calcite crystal polarizers could be used as polarizing beam splitters. Alternatively, a thin film polarizing beamsplitter may be better suited for the wavelengths of interest.

It should further be noted that if the EO switches (electro-optical polarization rotators) were eliminated and the last two polarizing beam splitters (122, 132) were replaced with a 50:50 splitter and a 67:33 splitter, respectively, the output beam 134 would be transmitted with 33% efficiency. This would be the limit of efficiency with a strictly passive beam combining scheme.

FIG. 2

Figure 2:
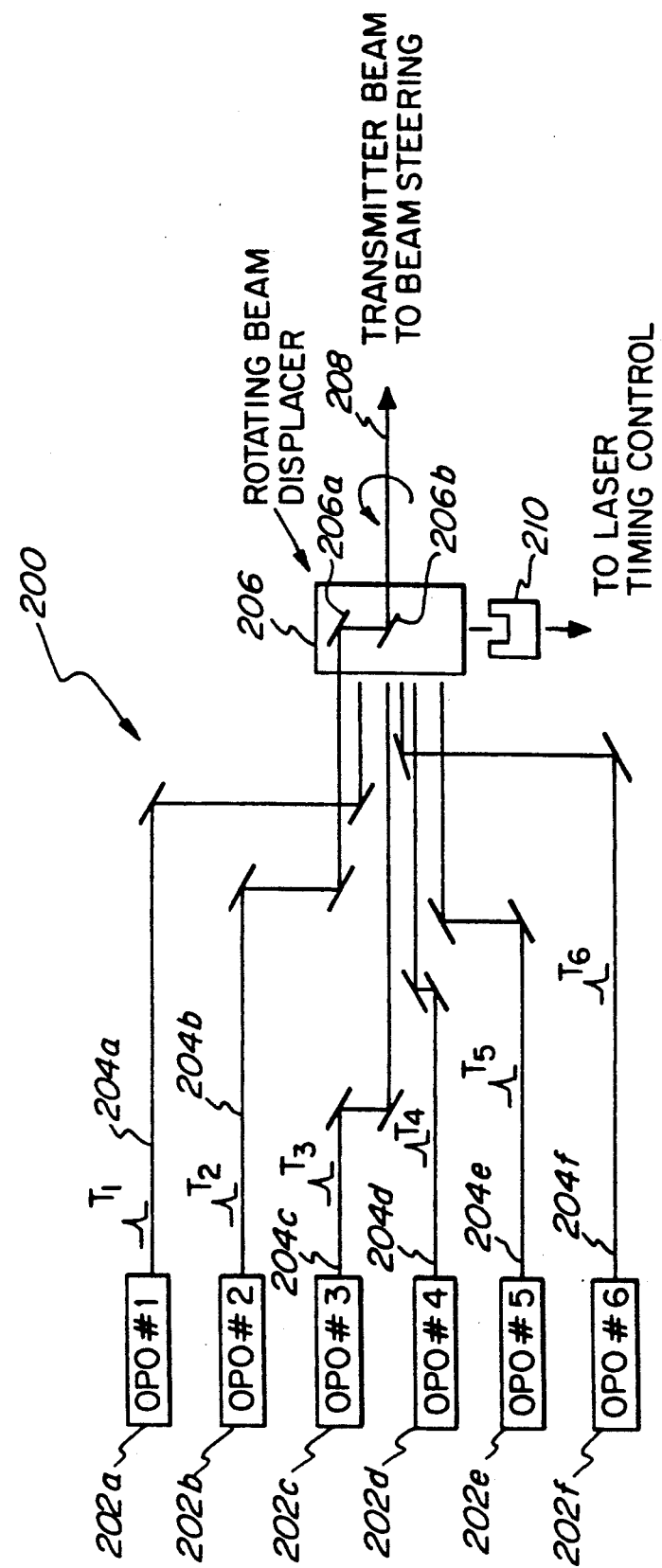
FIG. 2 is a schematic block diagram of a LIDAR transmitter employing fully time-multiplexed, mechanical beam switching, according to the present invention.

FIG. 2 shows an alternate, fully time-multiplexed transmitter 200 with a mechanical scanner acting as a switch to alternately send each beam down the transmitter axis. More particularly, six OPOs 202a, 202b, 202c, 202d, 202e and 202f each emit a pulsed beam 204a, 204b, 204c, 204d, 204e and 204f, at a time $T_1$, $T_2$, $T_3$, $T_4$, $T_5$ and $T_6$, respectively. The timing of these pulses may be the same as described with respect to FIG. 1.

The beams 204a through 204f are steered to be parallel with one another and distributed evenly (at 60 degree spacing) and at a given radius about a transmitter axis by beam steering mirrors. FIG. 2 shows two beam steering mirrors per beam to effect this purpose. In this manner the beams are adjusted to be accurately parallel in a "Gatling Gun" configuration, and are all directed at rotating beam displacer 206. The rotating beam displacer 206 rotates about the transmitter axis and contains two mirrors, one of which, the mirror 206a, is disposed at the radius of the incoming beams and the other of which, 206b, is disposed on the transmitter axis. By ensuring that the reflecting surfaces (mirrors 206a and 206b) of the rotating beam displacer 206 are kept accurately parallel, then the parallelism of the output beam 208 will not be affected by wobble of the beam displacer. Wobble will affect the offset between the beams, but that is much less important than the parallelism.

If it is acceptable to spread the timing of the six pulses over a 10 msec time, then the rotation rate of the beam displacer should be 6000 rpm. Since the rotation rate of the rotating beam displacer 206 may vary, a timing pickoff 210 is used to make fine corrections to the laser pulse timing ($T_1$, $T_2$, etc.) so that the timing of the individual beams (204a, 204b, etc.) precisely matches the rotational position of the beam displacer.

FIG. 3

Figure 3:
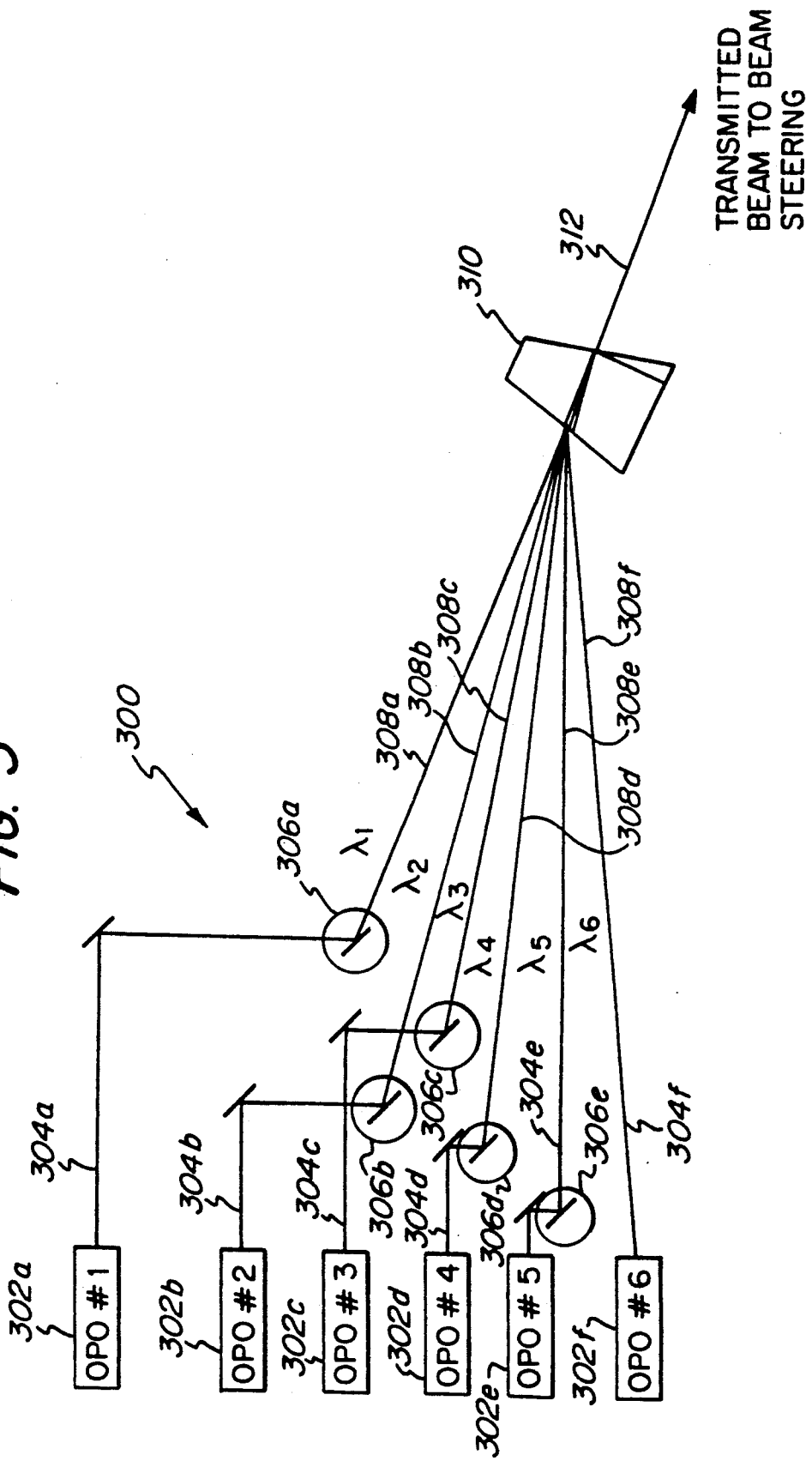
FIG. 3 is a schematic block diagram of a LIDAR transmitter employing wavelength multiplexing, according to the present invention.

FIG. 3 shows a wavelength-multiplexed transmitter 300 wherein a beam combiner uses the wavelength difference between the beams to combine them at high efficiency.

Six OPOs 302a, 302b, 302c, 302d, 302e and 302f generate output beams 304a, 304b, 304c, 304d, 304e and 304f at six different wavelengths. These beams may or may not be pulsed, since timing is not critical in this configuration. The beams may be continuous wave (CW).

The output beams 304a through 304f are directed, through appropriate mirrors to mirrors 306a, 306b, 306c, 306d, 306e and 306f that may be individually tilted and translated to provide the output beams along precise, specified paths 308a, 308b, 308c, 308d, 308e and 308f to a prism 310. The prism 310 may be made of germanium, fused silica or the like.

Because of the inherent differential refraction angle of the prism 310 at different wavelengths, the beams 308a through 308f, can be effectively combined into a single output beam 312.

This approach is appealingly simple if the wavelengths of the (laser) sources are fixed, but becomes considerably more complicated if the source wavelengths are to be tuned. Further, in this approach, there is no need to have time delays between the source pulses. Therefore, control of the lasers is somewhat simplified.

ATMOSPHERIC INTERROGATION

As discussed above, the output beam of any of the above-described transmitters 100, 200 or 300 may be directed through suitable optics to the atmosphere, whereupon it may be reflected by light hydrocarbons. Hereinafter are described receiver configurations for detecting the reflected beam ("return").

FIG. 4

Figure 4:
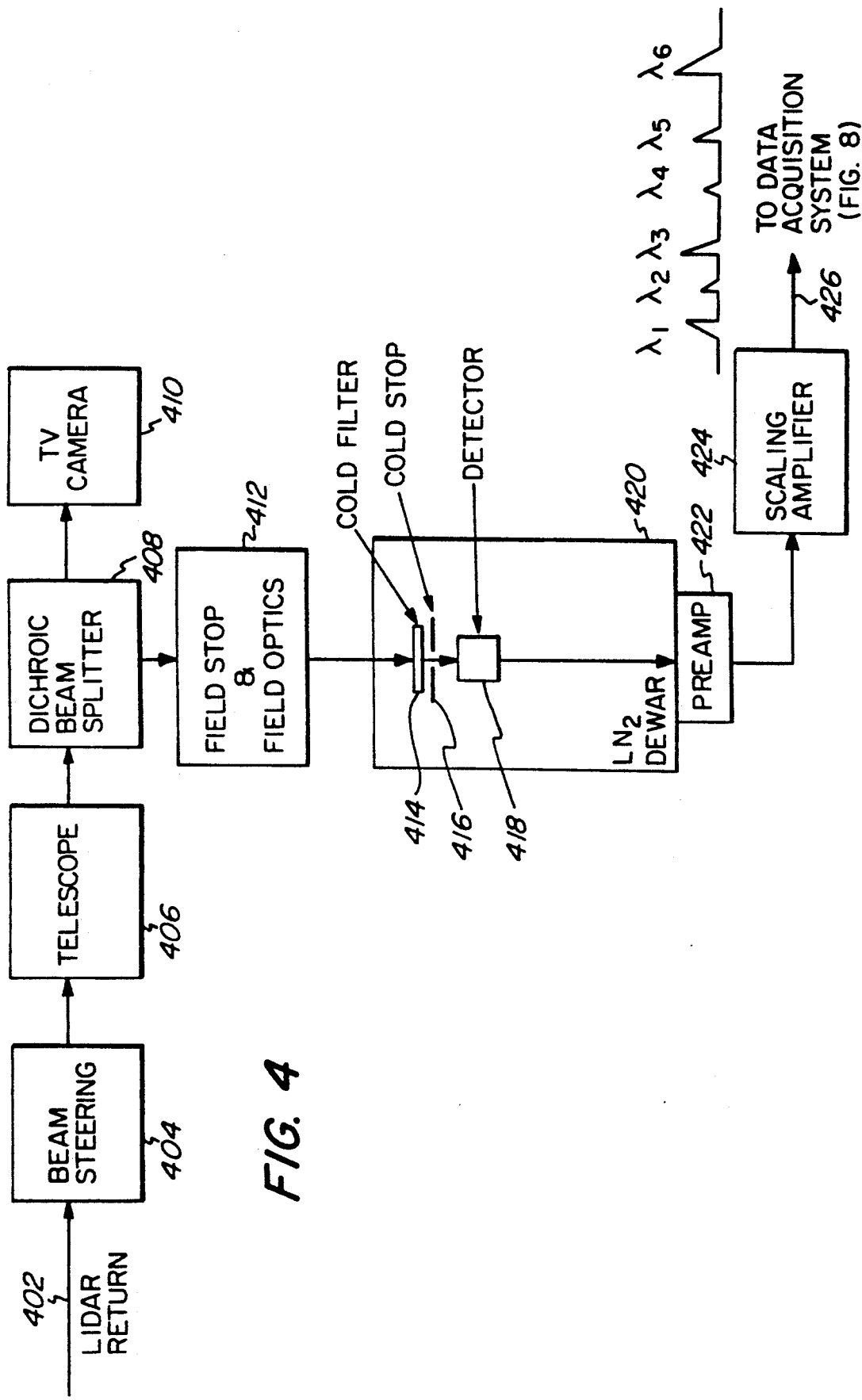
FIG. 4 is a schematic block diagram of a LIDAR receiver, fully time-multiplexed, according to the present invention.

FIG. 4 shows a fully time-multiplexed receiver configuration 400 for receiving the reflected output beams of the transmitters of FIGS. 1A or 2. From an optics viewpoint, this is the simplest possible receiver system. The source wavelengths can be tuned with impunity, since the encoding is in the pulse timing. More particularly:

The LIDAR return 402 is steered, through appropriate beam steering optics 404, through a telescope 406. From thence, the beam is directed to a dichroic beam splitter 408. One portion of the beam is directed to a TV camera 410 (sensitive to infrared radiation when operating with infrared returns) which is used to direct the beam steering mechanism 404. Another portion of the beam is directed by the beam splitter 408 to a field stop and field stop optics 412.

The return 402 is then provided, in sequence, to a cold filter 414, a cold stop 416 and a detector 418, all of which are contained within liquid nitrogen ($LN_2$) Dewar 420. The cold filter, cold stop and liquid nitrogen cooling of the detector are for limiting background noise.

Figure 8:
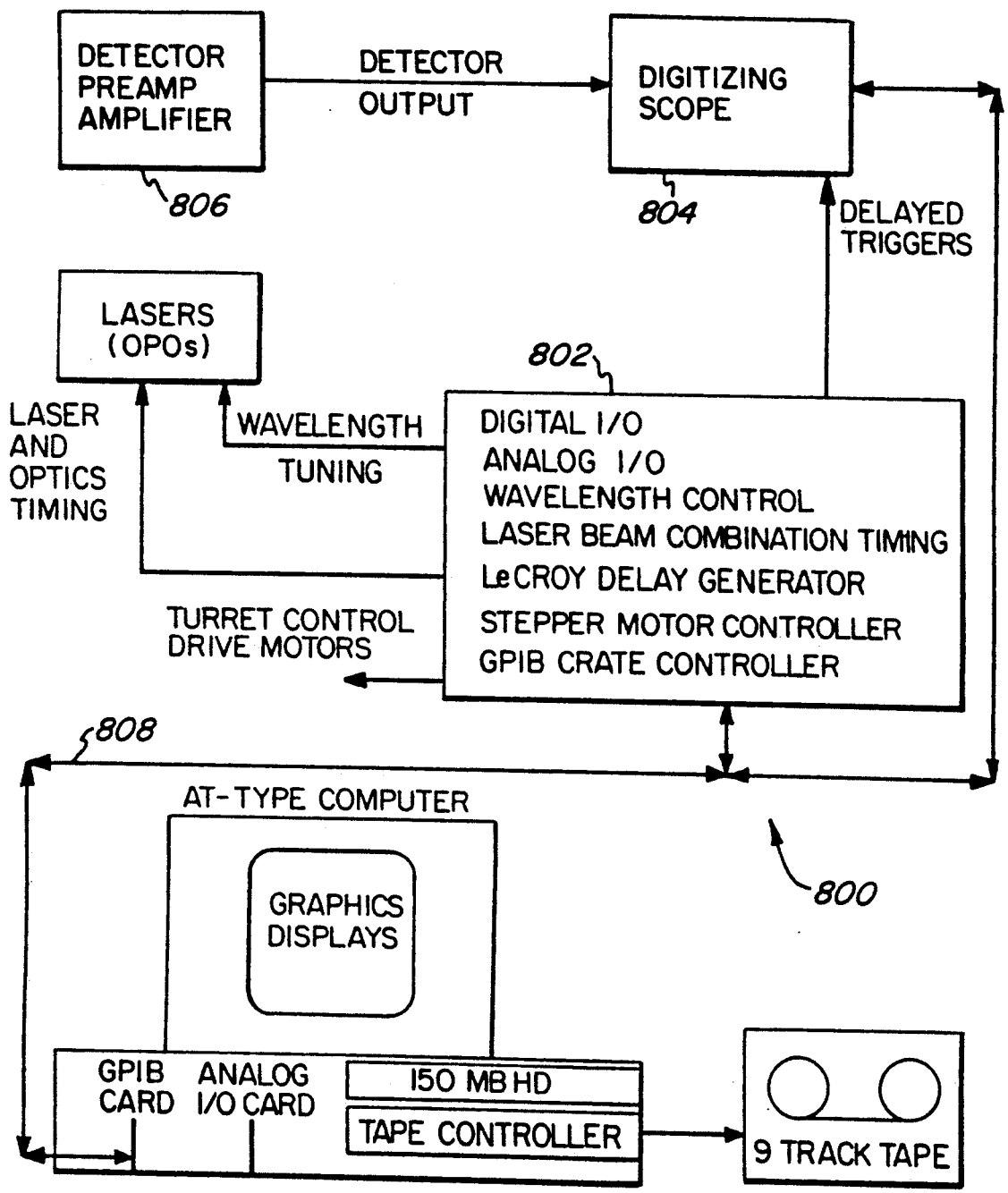
FIG. 8 is a system block diagram of the hardware configuration layout for the LIDAR system, single detector version (FIGS. 4 and 7), of the present invention.

The output of the detector 418 is provided to a preamplifier 422, thence to a scaling amplifier 424, which provides an output to the data acquisition system of FIG. 8. The output 426 contains time-sequenced pulses corresponding to the six wavelengths in the transmitted beam, as shown.

FIG. 5

Figure 5:
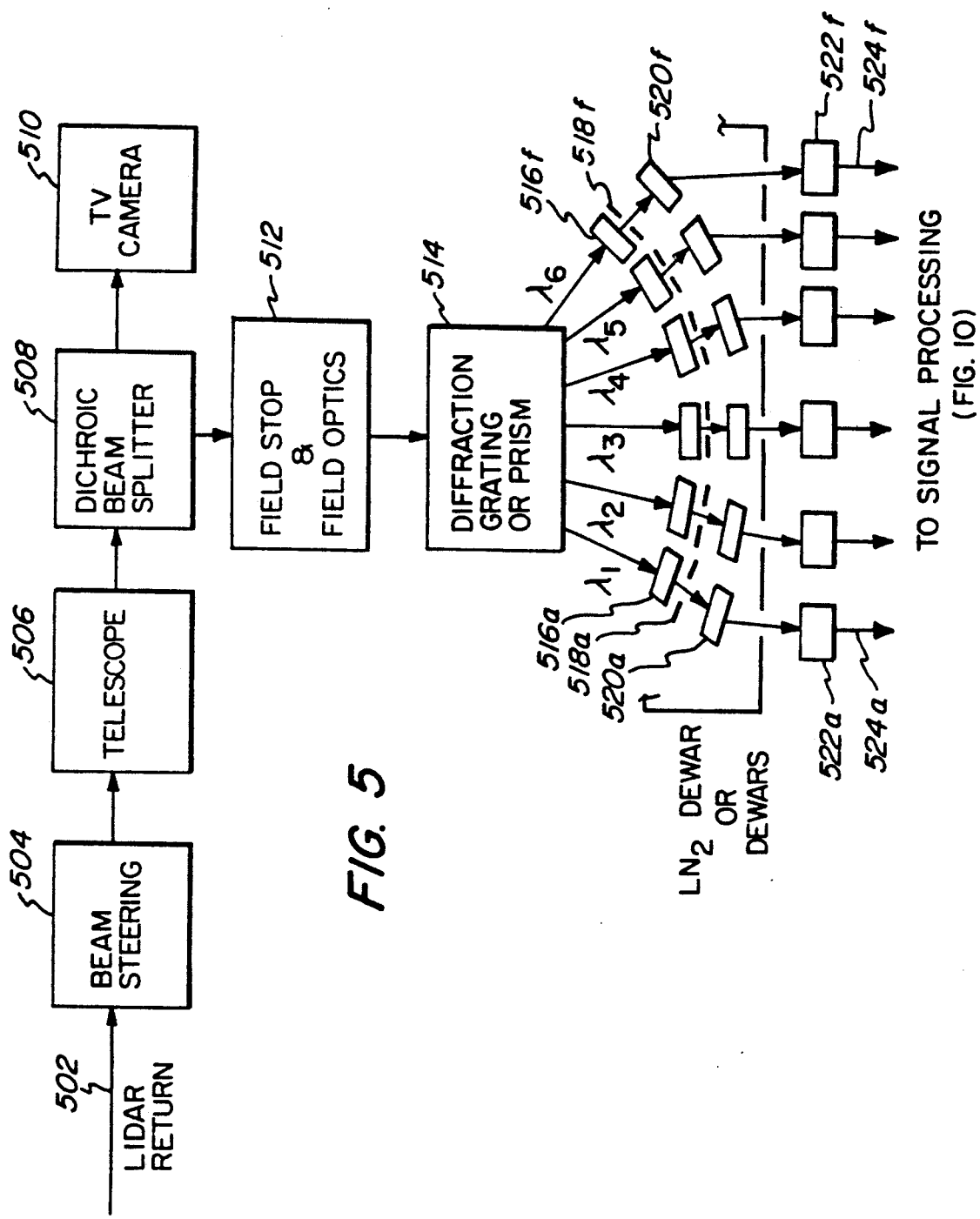
FIG. 5 is a schematic block diagram of a LIDAR receiver, wavelength-multiplexed, according to the present invention.

FIG. 5 shows a wavelength-multiplexed receiver 500 for receiving the reflected output beam of the transmitter 300 of FIG. 3.

In a manner similar to that described with respect to FIG. 4, the LIDAR return 502 is steered, through appropriate beam steering optics 504, through a telescope 506. From thence, the beam is directed to a dichroic beam splitter 508. One portion of the beam is directed to a TV camera 510 (sensitive to infrared radiation when operating with infrared returns) which is used to direct the beam steering mechanism 504. Another portion of the beam is directed by the beam splitter 508 to a field stop and field stop optics 512.

The return 502 is then provided to a diffraction grating or prism 514, which differentially refracts the various wavelength components of the return. These individual wavelength components of the return are each provided, in sequence, to a cold filter 516a through 516f, a cold stop 518a through 518f and a detector 520a through 520f, all of which are cooled in either a single large Dewar, or individual liquid nitrogen cooled Dewars, for the purposes described hereinbefore.

Figure 10:
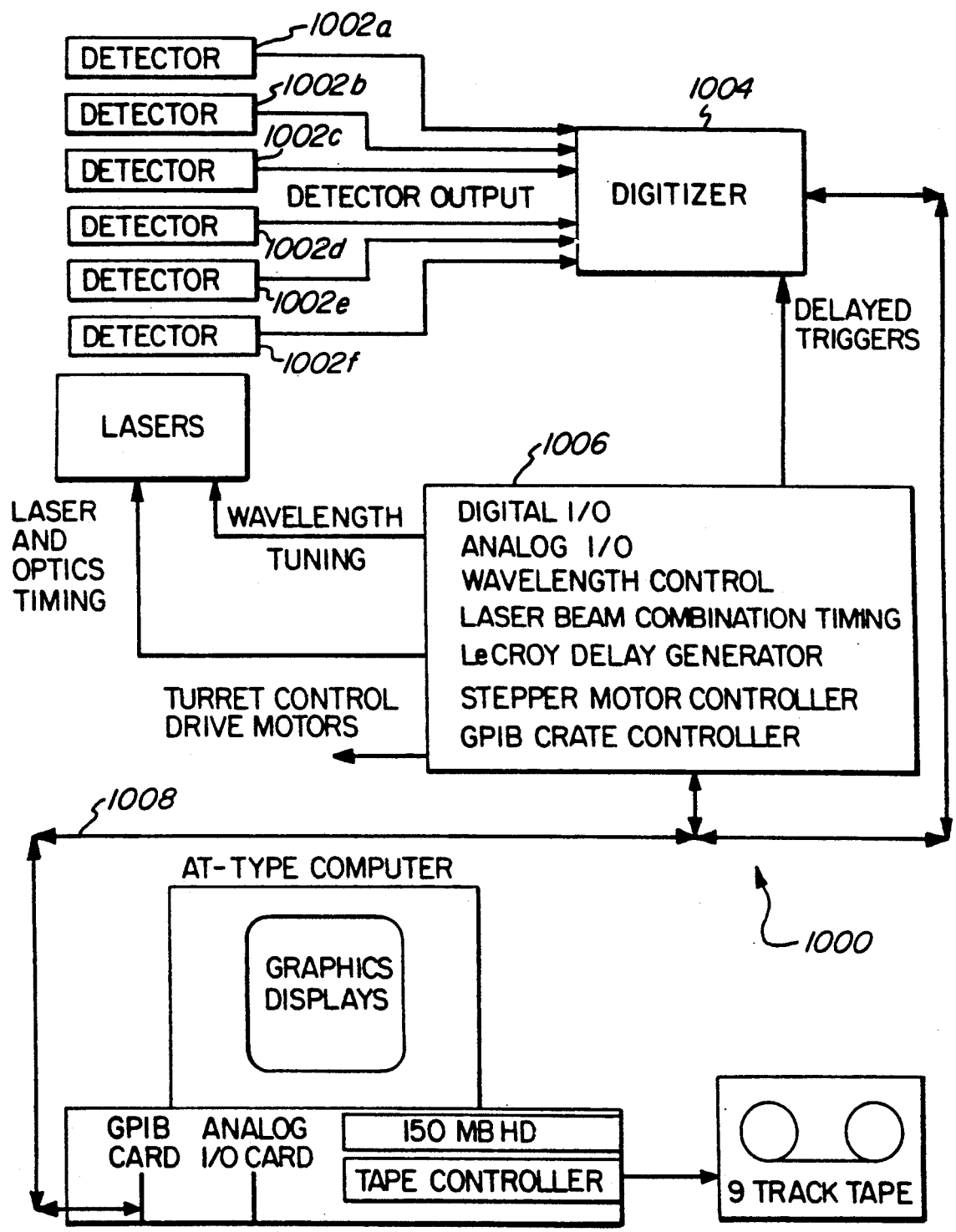
FIG. 10 is a system block diagram of the hardware configuration layout for the LIDAR system, multiple detector version (FIG. 5), of the present invention.

The outputs of the detectors provided through preamplifiers and scalers 522a through 522f (compare elements 422 and 424 of FIG. 4) to signal processing circuitry described in FIG. 10.

The wavelength-multiplexed receiver configuration is somewhat more complicated than the time multiplexed receiver because there are separate detectors for each wavelength. This can still be built ruggedly and quite simply if the wavelengths are fixed; in fact, an off-the-shelf detector array in a single Dewar can be used. However, as noted with respect to the transmitter configuration of FIG. 3, if the wavelengths are independently tunable, however, this scheme could quickly become too complex.

Adequate dispersion to separate the wavelengths is certainly obtainable. A preliminary calculation shows that using a 167 groove/mm grating (514) at a focal length of 250 mm will separate two laser lines 0.04 microns apart by 2 mm at the focal plane.

DETECTOR

The selection of a detector, especially for detecting LIDAR returns in the infrared region, cannot be done without a careful consideration of the system requirements. In the final analysis, to fully optimize the signal-to-noise ratio of a system, one must use a computer-based simulation because there are no analytical solutions for the optimum. However, it is possible to do an approximate analysis that will show the main features of the necessary tradeoffs and that will predict the system signal-to-noise ratio within a factor of three or so.

A good place to start is to examine the LIDAR signal to determine what parameters can be varied in the system design to maximize the signal. The instantaneous signal power at the detector is given by:

$$P(R) = P_o K \frac{A_R}{R^2} \frac{cT}{2} (R) \exp\left(-2 \int_o^R \sigma(r) dr\right) \quad (1)$$

In this equation, the parameters under control of the system designer are K, the efficiency of the LIDAR system ($K \leq 1$), $A_R$, the area of the LIDAR receiver aperture, and $P_o T$, the laser pulse energy.

The LIDAR return instantaneous power is proportional to the total energy transmitted in the laser pulse. That is, the instantaneous received power is independent of the length of the transmitted pulse. This means that the system signal-to-noise tradeoffs do not depend on the length of the transmitted pulse, which is a great simplification to the tradeoff analysis.

Besides making the system efficiency as high as possible, the only quantities that are practical to vary to optimize the system are the pulse energy and the area of the receiver aperture. Increases in the receiver area will almost always help the system signal-to-noise characteristics.

Thus, most of the system design decisions that affect the signal-to-noise ratio involve making the noise as small as possible.

For example, the system can be constructed with a receiving telescope having a 0.30 meter diameter aperture and a Field of View (FOV) of 200 microradians (full angle), which is about eight times the diffraction limit. This means that alignment between transmitter and receiver will be more difficult to achieve, but the background radiation will be lower, and more importantly a smaller detector can be employed. Of course this also means that the transmitter beam must be confined to this divergence angle.

These assumptions set the area - solid angle product at the detector. Taking a solid angle of 0.5 sr as being a practical limit, a detector having a diameter no smaller than 80 microns can be used.

The detector that has the highest quantum efficiency and adequate bandwidth for the aforementioned light hydrocarbon detecting purposes at 3 microns, and is preferably an InSb photodiode. These diodes are well known for their low noise characteristics.

The system noise will be limited by other factors. The quantum efficiency is quoted as 0.75, and the capacitance of an 80 micron diameter unit is about 5 pF. Since there will be some stray capacitance, a value of 10 pF is more realistic, which is about the practical limit if the preamplifier is not integrated with the detector.

For a given electrical bandwidth, the detector capacitance sets the maximum value of the load resistor. The noise sources in a detector preamplifier circuit (besides excess detector noise, if any) are: thermal noise of the load resistor, thermal noise of the detector shunt resistance, shot noise of the dark current, voltage noise of the preamplifier, and current noise of the preamplifier.

By using a transimpedance preamplifier, the bias voltage across the detector is kept to the desired value near zero, independent of background. Since the detector is being used in photovoltaic mode, there is no dark current.

FIG. 6

Figure 6:
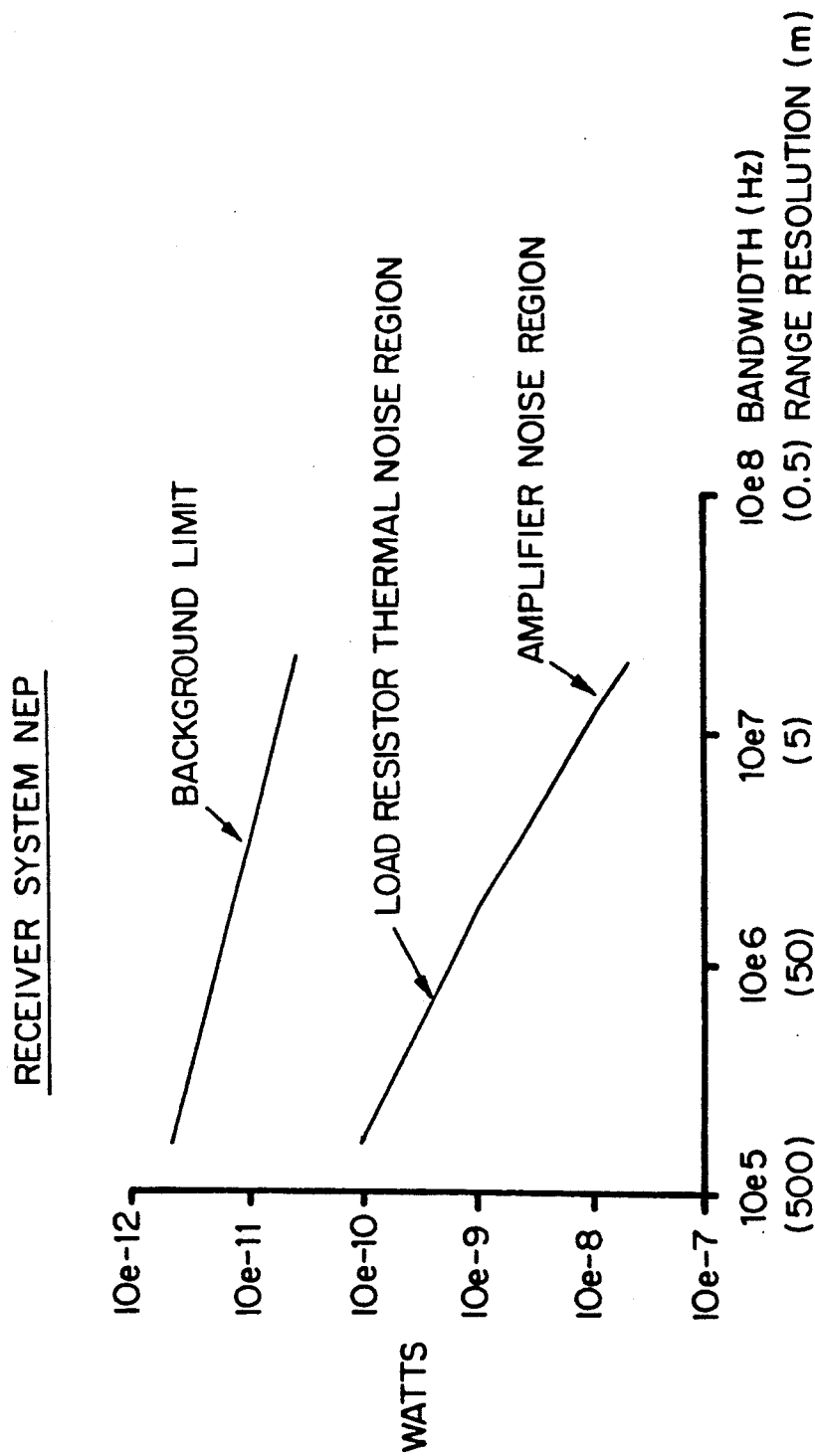
FIG. 6 is a graph indicating Noise Equivalent Power (NEP), and relates to the receiver configurations shown in FIGS. 4, 5, 7 and 10.

FIG. 6 shows a graph of Noise Equivalent Power (NEP) for the receiver systems of FIGS. 4 or 5. The vertical axis of the graph represents watts of NEP. Bandwidth and Range Resolution are indicated along the horizontal axis. It is immediately evident in this graphic representation, that the higher the bandwidth of the receiving system, the higher the potential for noise in the system.

The ultimate method of achieving low Noise Equivalent Power (NEP) is to use coherent detection, wherein the received signal is mixed with a local oscillator in the detector. Since the signal current depends on the product of the signal power and local oscillator power, the signal can be brought up out of the noise by increasing the local oscillator power. Even background noise can be overcome by this method. The theoretically achievable NEP is:

$$NEP_{coherent\ detection} \geq \frac{hc\ B}{\lambda \eta}$$

where is the quantum efficiency of the detector and h is Planck's constant. At 1 MHz bandwidth and 3.3 microns, this is $8 \times 10^{-14}$ watts at $\eta = 0.75$.

FIG. 7

Figure 7:
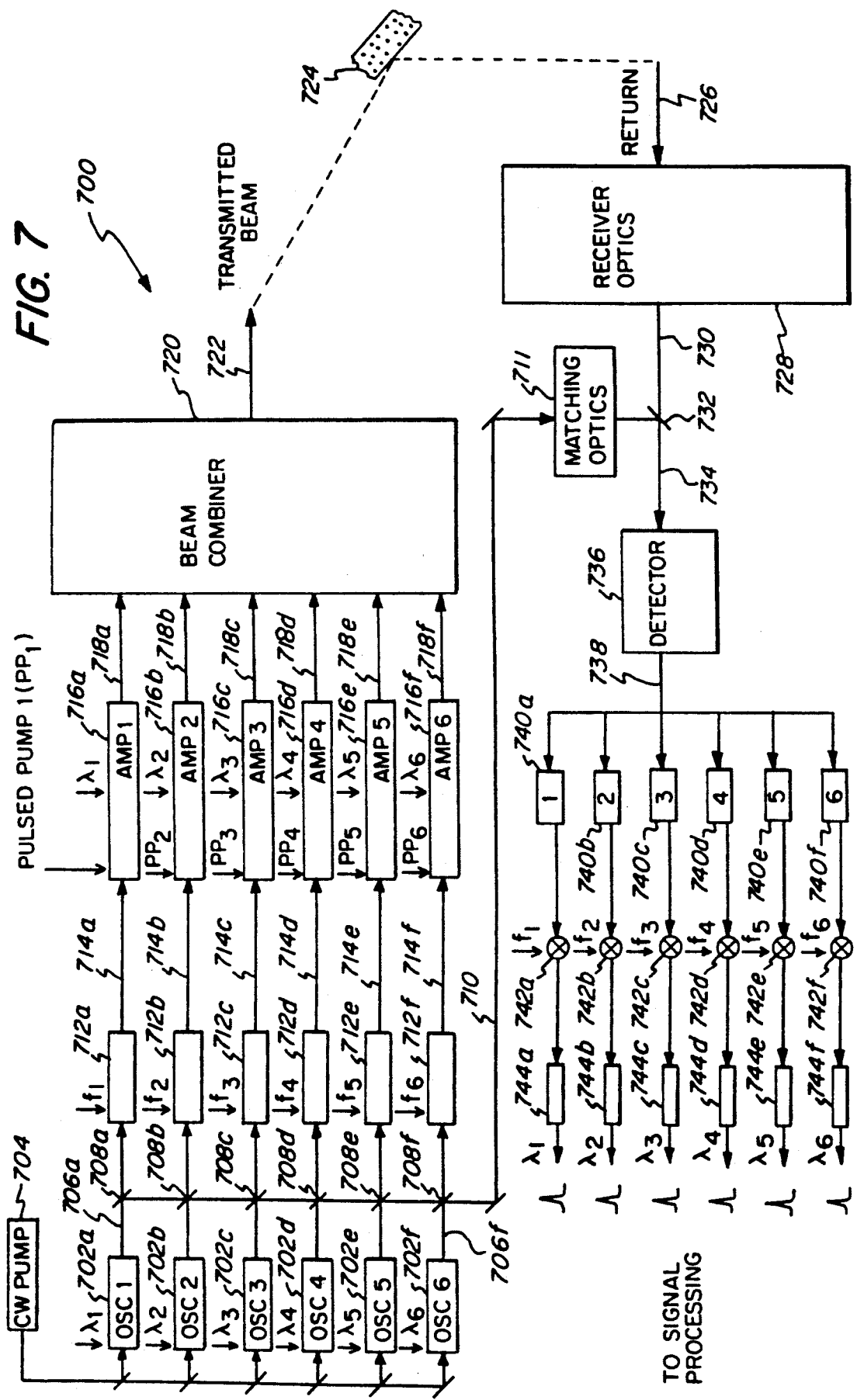
FIG. 7 is a schematic block diagram illustrating a coherent LIDAR system, according to the present invention.

FIG. 7 shows a coherent LIDAR system 700 applicable to the 3.3 micron wavelength region. In this system frequency modulation is used to encode the wavelengths, so that any of the previously presented beam combiners (FIGS. 1A, 2 or 3) can be used with a single detector receiver. The system uses cotuned OPO oscillators and amplifiers following the teachings of Baumgartner and Byer (Applied Optics 17, 3555, 1978). Output beams at distinct wavelengths are generated, and a different frequency shift is applied to each output beam by an acousto-optic modulator prior to its introduction to pulsed power amplifiers. On detection, the signals at the various wavelengths are separated by bandpass (IF) filters centered at the initially applied frequency offsets. The signals are then mixed down to baseband and lowpass filtered to produce the LIDAR return signals.

More particularly, in the transmitter section of the system, six OPO oscillators 702a, 702b, 702c, 702d, 702e and 702f are pumped by a CW (continuous wave) laser source 704. Mirrors are shown for directing the laser output to the OPOs. The OPOs 702a through 702f are individually tuned to produce output beams 706a through 706f at six discrete wavelengths (lambda$_1$ through lambda$_6$). A small portion, such as 3% of each output beam is directed by beamsplitters 708a through 708f along a single optical path 710 to the receiver portion of the system, discussed hereinafter. The remaining portions (97%) of the output beams are directed to respective acousto-optic modulators 712a through 712f, each of which is modulated at a distinct frequency f$_1$ through f$_6$. as shown.

The modulated output beams 714a through 714f are provided to OPO amplifiers 716a through 716f. These amplifiers are pulsed with pulsed pumps PP1 through PP5, and are tuned to the wavelength, or band, of the respective upstream OPO oscillator 702a through 702f. The timing of the pulses PP1 through PP5 is not critical in this modulated configuration.

The outputs 718a through 718f of the OPO amplifiers are provided to a beam combiner 720, which may be any of the beam combiners discussed hereinbefore (FIGS. 1A through 3), to provide a transmitted beam 722.

In the context of detecting light hydrocarbons in the atmosphere, the transmitted beam is used to interrogate a target area, represented by the element 724, which will produce a return (reflected beam) 726 according to the hydrocarbon concentration.

Turning now to the receiver portion of the system, the return 726 is collected by receiver optics 728 to form a beam 730. The aforementioned sample (3%) of the OPO oscillator output beams, on the optical path 710, is provided to matching optics 731 which scale the amplitude of the sample for introduction, through a mirror 732, to the received beam 730. This provides the optical analog of electrical "beat" frequencies in a composite beam 734, which will contain optical signals at the six sums and differences of the wavelengths of the OPO oscillator output beams 706a through 706f and their respective modulation frequencies f$_1$ through f$_6$.

The composite beam 734 is provided to a single detector 736, which may be a low cost, wideband photodetector, since it is only detecting the beat frequencies (lambda$_n$+/−f$_n$). The electrical output of the detector 736 is provided on a line 738 to six bandpass (IF) filters 740a through 740f, each of which is tuned to a respective one of the modulation frequencies f$_1$ through f$_6$ (used in the frequency shifters 712a through 712f, above). The output of each of the bandpass filters is provided to a respective mixer 742a through 742f, which receives as its other input the appropriate modulation frequency f$_1$ through f$_6$, as shown.

The output of each of the mixers 742a through 742f will contain a sum and a difference signal, wherein the difference signal is a voltage proportional to the amplitude of the received signal (return). The outputs of the mixers 742a through 742f are provided to respective lowpass filters 744a through 744f to remove the sum component of the signal. This leaves only the difference component as the output of the lowpass filter, which will represent the amplitude of the return at each of the OPO oscillator wavelengths. These signals are provided to signal processing circuitry, as described hereinafter (FIG. 8).

RECEIVER HARDWARE CONFIGURATION

FIG. 8 shows a hardware configuration layout for a single detector version of the LIDAR system.

FIG. 10 shows a hardware configuration layout for a multiple detector version of the LIDAR system.

Figure 9:
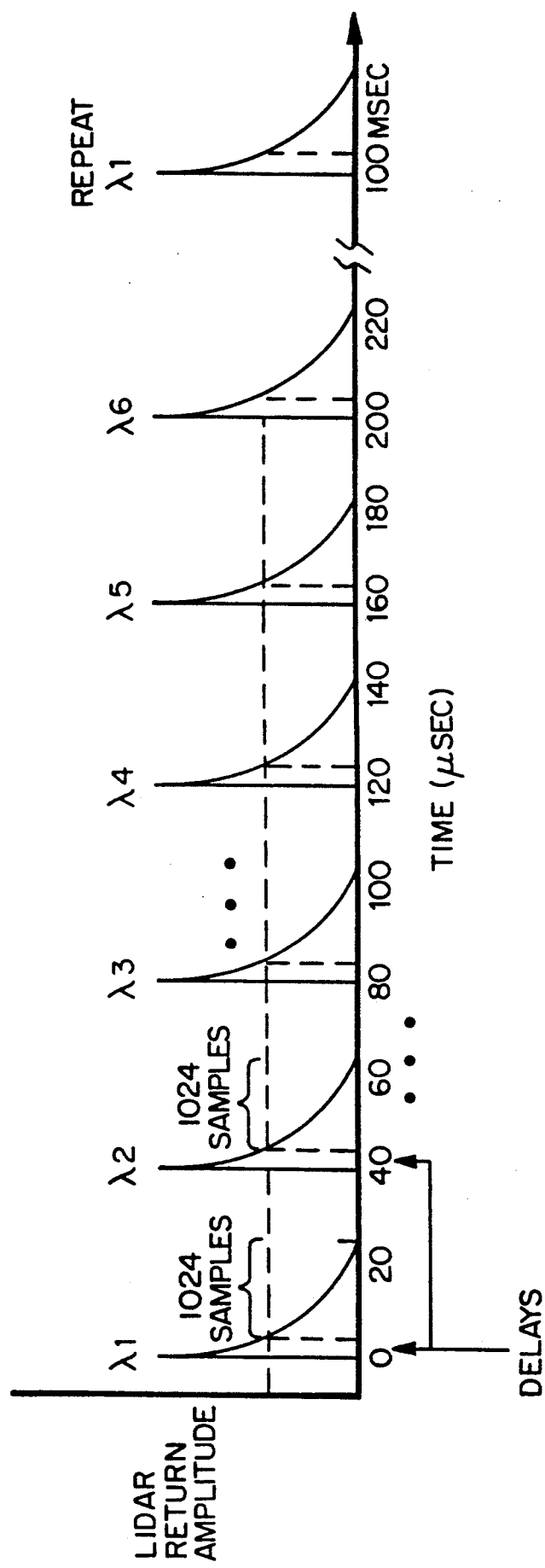
FIG. 9 is a timing diagram illustrating digitization of returns in the LIDAR system of FIGS. 8 and 10.

FIG. 9 shows a digitization timing diagram applicable to the hardware configurations of FIGS. 8 or 10.

In the system 800 of FIG. 8, a system controller 802, such as a KSC CAMAC crate, contains digital I/O circuitry, analog I/O circuitry, wavelength control circuitry, timing circuitry exercising control over the beam combiners (FIGS. 1A and 2), a delay generator such as a LeCroy delay generator, and a supervisory controller such as a GPIB crate controller. These components are well known to those skilled in the art to which this invention pertains, and are discussed only briefly herein.

The timing signals required to accurately digitize the LIDAR return signal are derived from the signals generated to control the LIDAR transmitter. Transmitter timing will involve the synchronization of the six laser sources (FIGS. 1A and 2), as well as aspects of combining the six different wavelength pulses into a single signal train. The required timing pulses will be derived from a single "start" pulse and will be generated by a dedicated circuit. The timing circuit must be accurate and it must be programmable.

The laser and optics timing signals (LIDAR transmitter timing signals) are also routed to the LeCroy delay generator. The six individual laser firing pulses are AND gated into a composite pulse train. This composite pulse train is delayed by the delay generator and forms a train of trigger pulses for the digitizing scope 804. A suitable digitizing scope is the Tektronix RTD 710, rated at 100 MHz.

The single detector 806 will work well with a digitizer that is capable of digitizing the incoming LIDAR return signal and processing it for easy transfer to the host computer. The Tektronix RTD710 Programmable Waveform Digitizer is recommended.

With reference to FIG. 10, in a system with individual detectors 1002a through 1002f for each laser wavelength, a multi-channel digitizer 1004 will be required in lieu of the digitizing scope (804 of FIG. 8). AaLeCroy Model 2262 digitizer is suitable for this purpose. It has four input channels and typically resides in the CAMAC crate 1006. Two such units would handle the six channel system.

The Tektronix RTD710 Programmable Waveform Digitizer (804; FIG. 8) is a high resolution transient waveform digitizer for capturing signals containing frequency components up to 100 MHz. The pulses illustrated in FIG. 9 are digitized into 1024 samples each during the 20-microsecond pulse duration. The required sample rate of 51.2 MHz is well within the capabilities of the RTD710.

The RTD710 provides flexibility in partitioning its storage memory to suit a variety of acquisition applications. For this design the record length is set to 1024 words. The digitizer can capture 64 such records using its Auto Advance Recording mode. Here, each trigger pulse causes the incoming data to be stored to a predefined memory segment. Each succeeding trigger pulse causes the digitizer to switch to a new memory segment, where the incoming data points are stored. Using this feature of the RTD710, the returns from each laser pulse are stored in separate memory segments. The primary advantage of this scheme is that each individual laser pulse generates its own set of data points. The trigger delay time (generated by the LeCroy delay generator) is the same for each pulse, making all of the return records symmetrical in time.

The Tektronix digitizer is programmable via the GPIB interface, and the captured data can be transferred in blocks to the host computer via the GPIB interface at rates exceeding 250 Kbytes per second.

For the multiple detector scheme (FIG. 10), the LeCroy Model 2262 would be used to capture multiple pulses simultaneously at 80 MSample per second. Its 40 Mhz bandwidth and 10 bit resolution are similar to the specs on the Tektronix RTD710. It is also programmable via the GPIB. It will fulfill the multi-channel requirement if it becomes necessary.

As seen in the timing diagram (FIG. 9), the individual laser pulses would be separated by 40 microseconds. The series of six pulses are repeated at 100 millisecond intervals. In the time between shots, the host computer must coordinate a number of activities. These include:
command the turret to the next position
commanding the block transfer of the digitized data
processing and displaying the previous frame's data
archiving (to disk) the previous frame's data.

The data captured by the host computer 802 (FIG. 8) or 1006 (FIG. 10) is provided over a bus 808 (FIG. 8) or 1008 (FIG. 10), which in these illustrative hardware embodiments would be an IEEE 488 GPIB bus, to an AT-type computer. Software for control of these functions is straightforward, and is well within the skill of one skilled in the art to implement, according to the specific uses to which the invention may be put.

What is claimed is:

1. A method of detecting light hydrocarbons in the atmosphere, comprising the following steps:
generating at lest two pairs of pulsed polarized beams by optical parametric oscillation with at least two tunable coherent light sources, each beam tuned to a different wavelength, each pair of beams having a common polarization state;
directing the polarized beams so that they are substantially located on a common optical axis;
transmitting the beams into the atmosphere;
receiving returns from light hydrocarbons in the atmosphere; and
analyzing the returns to determine the light hydrocarbon content in the atmosphere.

2. A method as defined in claim 1, wherein the pairs of beams are directed substantially along the common optical axis with a polarization combining beam splitter.

3. A method as defined in claim 1, wherein at least one pair of polarized beams has a different polarization state than at least one other pair of polarized beams.

4. Method according to claim 1 wherein:
the wavelengths of the pulsed beams are in the 3.1 to 3.5 micron range.

5. Method according to claim 4, wherein:
the wavelengths of at least two of the pulsed beams are in the 3.16 to 3.18 micron range.

6. Method according to claim 4, wherein:
the wavelengths of at least two of the pulsed beams are in the 3.37 to 3.5 micron range.

7. Method according to claim 1, wherein:
the wavelengths of at least two of the pulsed beams are in the 2.0 to 2.4 micron range.

8. A method of detecting light hydrocarbons in the atmosphere, comprising the following steps:
generating a plurality of beams with a plurality of coherent light sources, each beam having a different wavelength;
reflecting each beam along a predetermined path into a prism;
combining the beams in the prism and transmitting a single transmitting beam from the prism;
transmitting the single transmitting beam into the atmosphere;
receiving returns from light hydrocarbons in the atmosphere; and
analyzing the returns to determine the light hydrocarbon content in the atmosphere.

9. A method as defined in claim 8, wherein each beam is generated by optical parametric oscillation.

* * * * *